United States Patent [19]

Beatty

[11] Patent Number: 5,741,955
[45] Date of Patent: Apr. 21, 1998

[54] PROCESS FOR REDUCTIVE HYDROLYSIS OF NITRILES

[75] Inventor: Richard Paul Beatty, Newark, Del.

[73] Assignee: E. I. du Pont de Nemours and Company, Wilmington, Del.

[21] Appl. No.: 544,227

[22] Filed: Oct. 17, 1995

Related U.S. Application Data

[63] Continuation-in-part of Ser. No. 381,597, Jan. 31, 1995, abandoned.
[51] Int. Cl.$^6$ .................. C07D 307/28; C07C 31/38; C07C 31/20; C07C 31/125
[52] U.S. Cl. .................. 568/842; 558/451; 568/852; 568/902; 549/295
[58] Field of Search .................. 558/451; 568/842, 568/852, 902; 549/295

[56] References Cited

U.S. PATENT DOCUMENTS

| | | | |
|---|---|---|---|
| 3,454,644 | 7/1969 | Dewhirst | 564/385 |
| 4,482,760 | 11/1984 | Kleeman et al. | 568/811 |
| 4,810,825 | 3/1989 | Matsushita et al. | 568/840 |
| 5,057,581 | 10/1991 | Rempel et al. | 525/338 |
| 5,208,296 | 5/1993 | Rempel et al. | 525/338 |

FOREIGN PATENT DOCUMENTS 4-36250  2/1992  Japan .

OTHER PUBLICATIONS

Takenaka Shinji et al., Production of Aldehydes and Alcohols, *Patents Abstracts of Japan*, 16, 207, 1992.

W. Jung et al., *Liebigs Annalen Der Chemie*, 12, 1952–1959, 1979.

Moers, F.G. et al, *Recueil*, 91, 591 (1972).

Esteruelas and Werner, *J. Organomet. Chem.*, 303, 221 (1986).

Gusev, D.G. et al, *Inorg. Chem.*, 31(1), 2–4 (1992).

Dehmlow, E.V., *The Kirk-Othmer Encyclopedia of Chemical Technology*, 4th Ed., vol. 5, pp. 374–383 (1993).

Grushin, V.V., *Acc. Chem. Res.*, 26, 279 (1993).

Mizzoni, R.H. et al, *J. Med. Chem.*, 13(5), 878 (1970).

Meyer et al, *Chem. Ber.*, 123(4), 697–702 (1990).

Esteruelas et al, *J. Mol. Catalysis*, 53, 43–52 (1989).

Larock, Comprehensive Organic Transformations—A Guide to Functional Group Preparations, VCH Publishers Inc., New York, New York, 1989, p. 483.

*Primary Examiner*—Johann Richter
*Assistant Examiner*—Laura L. Stockton

[57] ABSTRACT

This invention concerns processes for the reductive hydrolysis of nitriles to alcohols utilizing as a catalyst a transition metal complex of the formula $MHZ(CO)L_n(PR_3)_2$ wherein: M is a transition metal selected from the group consisting of: Fe, Ru and Os; Z is an anionic ligand; L is a neutral ligand; n is 0 or 1; and $PR_3$ is a phosphine ligand.

21 Claims, No Drawings

PROCESS FOR REDUCTIVE HYDROLYSIS OF NITRILES

CROSS-REFERENCE TO RELATED APPLICATION

This is a continuation-in-part of application Ser. No. 08/381,597 filed Jan. 31, 1995 now abandoned.

FIELD OF THE INVENTION

This invention concerns processes for the reductive hydrolysis of nitriles to alcohols, including reductive hydrolysis of mononitriles to primary alcohols, selective reductive hydrolysis of dinitriles to hydroxynitriles and the reductive hydrolysis of dinitriles to diols.

TECHNICAL BACKGROUND

Japanese Patent Application, Publication Kokai:Hei 4-36250 (a992) describes the hydrogenation of nitriles in the presence of water using heterogeneous catalysts. Yields and selectivities were not very high. Example 1 of Hei 4-36250 showed that when benzonitrile was hydrogenated using Raney Ni (50° C., 1 atm), at 75% benzonitrile conversion, the selectivity to benzyl alcohol was only 51%; 23% of the benzonitrile converted formed benzylamine.

SUMMARY OF THE INVENTION

The present invention provides a process for the reductive hydrolysis of mononitriles to alcohols, the selective reductive hydrolysis of dinitriles to hydroxynitriles and the reductive hydrolysis of dinitriles to diols in the presence of a transition metal complex of the formula $$MHZ(CO)L_n(PR_3)_2$$

wherein:

M is a transition metal selected from the group consisting of: Fe, Ru and Os;

Z is a formally anionic ligand selected from the group consisting of: H, halogen, R, C(O)R, OC(O)R, CO$_2$R, CN, NR$_2$ and OR;

L is a neutral ligand selected from the group consisting of: H$_2$; N$_2$; CO; a monofunctional compound selected from the group consisting of: nitriles, amines, alcohols, ethers, esters, amides, alkenes, alkynes, aldehydes, ketones and imines; and a multifunctional compound containing at least two functional groups independently derived from the monofunctional compounds;

(PR$_3$)$_2$ represents phosphine ligands present as either separate ligands or cojoined together;

each R is a substituent independently selected from the group consisting of: H; and a hydrocarbyl group, optionally substituted with one or more halo, hydrocarbyloxy, hydrocarbylamino or dihydrocarbylamino groups; and n is 0 or 1.

This invention provides a process for the reductive hydrolysis of an organic nitrile, comprising the steps of:

(a) contacting said nitrile with gaseous hydrogen and water in the presence of a catalyst having the formula MHZ(CO)L$_n$(PR$_3$)$_2$ as defined above; and (b) subsequently agitating the nitrile, water, hydrogen and catalyst to form an alcohol.

This invention provides a process for the selective reductive hydrolysis of a dinitrile, comprising the steps of:

(a) contacting said dinitrile with gaseous hydrogen and water in the presence of a catalyst having the formula MHZ(CO)L$_n$(PR$_3$)$_2$ as defined above;

(b) subsequently agitating the dinitrile, hydrogen, water and catalyst for an amount of time selected to favor yield of a hydroxynitrile over yield of a diol.

DETAILED DESCRIPTION OF THE INVENTION

The reductive hydrolysis and selective reductive hydrolysis processes of the present invention concern the use of transition metal complexes of the formula MHZ(CO)L$_n$(PR$_3$)$_2$ wherein:

M is a transition metal selected from the group consisting of: Fe, Ru and Os;

Z is a formally anionic ligand selected from the group consisting of: H, halogen, R, C(O)R, OC(O)R, CO$_2$R, CN, NR$_2$ and OR;

L is a neutral ligand selected from the group consisting of: H$_2$; N$_2$; CO; a monofunctional compound selected from the group consisting of: nitriles, amines, alcohols, ethers, esters, amides, alkenes, alkynes, aldehydes, ketones and imines; and a multifunctional compound containing at least two functional groups independently derived from the monofunctional compounds;

(PR$_3$)$_2$ represents phosphine ligands present as either separate ligands or cojoined together;

each R is a substituent independently selected from the group consisting of: H; and a hydrocarbyl group, optionally substituted with one or more halo, hydrocarbyloxy, hydrocarbylamino or dihydrocarbylamino groups; and n is 0 or 1.

By hydrocarbyl is meant a straight-chain, branched, or cyclic arrangement of carbon atoms connected by single, double, or triple carbon-to-carbon bonds and substituted accordingly with hydrogen atoms. Hydrocarbyl groups can be aromatic and/or aliphatic, for example, alkyl, cycloalkyl, alkenyl, cycloalkenyl, alkynyl, aryl, alkylaryl and aralkyl. Optionally, the hydrocarbyl group in addition to substitution with hydrogen atoms can have substitution with halogen such as fluorine, chloride, bromine or iodine atoms. The hydrocarbyl group can also be substituted with hydrocarbyloxy, hydrocarbylamino or dihydrocarbylamino, such as dimethylamino or pyridyl, groups. Suitable hydrocarbyl groups can be methyl, ethyl, propyl, isopropyl, butyl, isobutyl, tert-butyl, octylcyclopropyl, cyclobutyl, cyclopentyl, methylcyclopentyl, cyclohexyl, methylcyclohexyl, benzyl, phenyl, napthyl, o-tolyl, m-tolyl, p-tolyl, xylyl, vinyl, allyl, butenyl, cyclohexenyl, and cyclooctenyl. Suitable substituted hydrocarbyl groups can be β-methoxyethyl, 4-methoxybutyl, 2-pyridyl, 4-trifluoromethylphenyl, 4-(N,N-dimethylamino)butyl, and 2-ethoxy-1-(2-pyridyl)ethyl.

Representative phosphine ligands are cyclohexylphosphine, phenylphosphine, diethylphosphine, dicyclohexylphosphine, diphenylphosphine, trimethylphosphine, triethylphosphine, tri-n-propylphosphine, tri-isopropylphosphine (P-iPr$_3$), tri-n-butylphosphine, tri-isobutylphosphine, tri-t-butylphosphine, triphenylphosphine, tricyclohexylphosphine (PCy$_3$), tribenzylphosphine, tris(2-pyridyl)phosphine, tri-p-tolylphosphine, tris(p-trifluoromethylphenyl)phosphine, o-diphenylphosphino-N,N-dimethylaniline, (3-N,N-dimethylaminopropyl)di-isopropylphosphine, (4-N,N-dimethylaminobutyl)di-isopropylphosphine, diphenylmethylphosphine, dimethylphenylphosphine, dicyclohexyl(β-methoxyethyl)phosphine, bis(β-methoxyethyl)phenylphosphine, and 1-(diphenylphosphino)-2-ethoxy-1-(2-pyridyl)ethane.

Two or more phosphine ligands can be cojoined, forming diphosphines, triphosphines, or even higher polyphosphines. Examples of such cojoined ligands comprise 1,2-bis(dimethylphosphino)ethane, 1,2-bis(diethylphosphino)ethane, 1,2-bis(dicyclohexylphosphino)ethane, bis(dicyclohexylphosphino)methane, 1,2-bis[(β-methoxyethyl)phosphino]ethane, 1,2-bis(diphenylphosphino)ethane, 1,3-bis(diphenylphosphino)propane, 1,4-bis(diphenylphosphino)butane, 1,2-bis(diphenylphosphino)benzene, (−)-1,2-bis((2R, 5R)-2,5-dimethylphospholano)benzene, (R)-(+)-2,2'-bis(diphenylphosphino)1,1'-binapthyl, bis(2-diphenylphosphinoethyl)phenylphosphine, tris(2-diphenylphosphinoethyl)phosphine, and 1,1,1-tris(diphenylphosphinomethyl)ethane.

Phosphine ligands can also be attached to various polymer supports. Examples comprise triphenylphosphine-on-styrene-divinylbenzene copolymers sold by Strem and Aldrich and triorganophosphine-functionalized polysiloxanes. Many other similar appropriate supports are known.

Bulky phosphine ligands with cone angles greater than 140°, such as P-iPR$_3$ and PCy$_3$ are preferred.

Suitable Z formally anionic ligands can be H; halogen, such as fluorine, chlorine, bromine and iodine atoms; R, C(O)R; OC(O)R; CO$_2$R, CN, NR$_2$, or OR, wherein R is as defined above.

Representative examples of Z groups comprise —OH, alkoxy such as —OCH$_3$, phenoxy such as —OC$_6$H$_5$, —OCH$_2$CH$_2$OCH$_3$, —NMe$_2$, —NEt$_2$, —CH$_3$, n—C$_4$H$_9$ and —C≡C—Ph, wherein Me is methyl, Et is ethyl and Ph is phenyl.

Suitable L neutral ligands can be H$_2$; N$_2$; CO; a monofunctional compound selected from the group consisting of: nitriles, amines, alcohols, ethers, esters, amides, alkenes, alkynes, aldehydes, ketones and imines; or a multifunctional compound containing at least two functional groups independently derived from the monofunctional compounds. For example, NH$_2$CH$_2$CH$_2$CH(COOR)CH$_2$OH is a multifunctional compound as it contains at least two functional groups derived from the monofunctional compounds amine, ester and alcohol. Suitable 2-electron donor L ligands, which are well known to those skilled in the art, are described in Principles and Applications of Organotransition Metal Chemistry by J. P. Collman et al., University Science Books, Mill Valley, Calif. (1987), chapters 2 and 3. Also known in the art are multidentate ligands wherein at least one L is cojoined with at least one PR$_3$, such as the previously mentioned PR$_3$ ligands, such as dicyclohexyl(beta-methoxyethyl)phosphine and 1-(diphenylphosphino)-2-ethoxy-1-(2-pyridyl)ethane. The preferred L are those molecules containing fully saturated Lewis basic donors, namely, amines, alcohols, and ethers. Less preferred are molecules containing unsaturated, potentially hydrogenatable Lewis base donors, such as, alkenes, alkynes, aldehydes, ketones, nitriles, imines, and esters. These unsaturated molecules can be used, but can be partially or completely hydrogenated in the course of preparing the ruthenium complex according to the current invention or while the complex is subsequently used in a reductive hydrolysis reaction. Notwithstanding the above discussion, preferred L also can be the substrates, intermediates, and products of reductive hydrolysis; for example, in the case of an adiponitrile reductive hydrolysis, adiponitrile, 6-hydroxycapronitrile, 1,6-hexanediol, 6-aminocapronitrile, and 6-aminohexanol are all preferred ligands. Representative examples of suitable L are amines such as butylamine and hexamethylenediamine, ethers such as tetrahydrofuran and t-butyl methyl ether, nitriles such as butyronitrile or adiponitrile, esters such as ethyl acetate or dimethyl adipate, and amides such as N,N-dimethylacetamide.

Complexes wherein M is Ru, and Z is H or halogen are preferred. Of those preferred complexes, when n is 1, L is preferably H$_2$.

Complexes wherein M is Ru, Z is H or halogen, n is 0 or n is 1 and L is H$_2$, and (PR$_3$)$_2$ are bulky phosphine ligands with cone angles greater than about 140°, such as RuHCl(CO)(P-iPr$_3$)$_2$, RuHCl(CO)(PCy$_3$)$_2$, RuH$_2$(H$_2$)(CO)(P-iPr$_3$)$_2$, and RuH$_2$(H$_2$)(CO)(PCy$_3$)$_2$ are especially preferred.

Many of the transition metal complexes useful as catalysts in the processes of the present invention can be prepared according to procedures set forth in the art. For example, Esteruelas and Werner, J. Organomet. Chem., 1986, 303, 221 prepared RuHCl(CO)(PiPr$_3$)$_2$ by refluxing RuCl$_3$(H$_2$O)$_x$ and P-iPr$_3$ over a period of a few hours, allowing the product to settle and then collecting on a frit.

Various other RuHZ(CO)(L)(PR$_3$)$_2$ complexes are known in the art, for example, those described by Rempel et al. in U.S. Pat. No. 5,208,296 and U.S. Pat. No. 5,057,581; U. Meyer, H. Werner, Chem. Ber., 123(4), 697 (1990), Esteruelas et al., J. Mol. Catalysis, 53, 43 (1989) and references therein. A wide variety of RuHZ(CO)(L)(PR$_3$)$_2$ can be prepared, or formed in situ, by addition of neutral 2-electron donor ligands to ruthenium precursors such as RuHZ(CO)(PR$_3$)$_2$, which are coordinatively unsaturated and can readily add such as ligand.

RuHZ(CO)(L)(PR$_3$)$_2$ wherein L is a substrate, intermediate, or product of the reductive hydrolysis reaction are particularly preferred since they may be used as catalysts without introducing extraneous ligands to the process, thereby simplifying the process and minimizing cost.

Such substrates, intermediates, or products can be simple hydrocarbyl nitriles such as capronitrile, with no other functionality present, or can be very complicated multifunctional molecules such as those encountered in agricultural and pharmaceutical syntheses. The great value of reductive hydrolysis stems from the fact that the nitrile group is one of the most versatile in organic chemistry. It can be introduced with great precision, including stereospecificity (for example by the use of asymmetric hydrocyanation catalysts), so that a wide range of very complex organic structures can be constructed containing carefully placed nitrile groups. For example, alpha-methyl-6-methoxy-2-naphthaleneacetonitrile contains a methoxy substituent in addition to the nitrile and can be reductively hydrolyzed to the corresponding alcohol, a molecule related to the important nonsteroidal antiinflammatory drug, 2-(6-methoxy-2-naphthalene)propionic acid. Single enantiomers of this nitrile can be synthesized in high purity (e.g. see Casalnuovo et l. U.S. Pat. No. 5,175,335), and reductively hydrolyzed with good retention of configuration.

The process of the present invention for the reductive hydrolysis of an organic nitrile comprises contacting the nitrile with gaseous hydrogen and water in the presence of a catalyst having the formula, MHZ(CO)L$_n$(PR$_3$)$_2$, as described above. Subsequently, the nitrile, water, hydrogen and catalyst are agitated to form an alcohol. The reductive hydrolysis of a dinitrile to form a diol is one embodiment of this process.

Previously known catalysts for reductive hydrolysis reactions typically yield only low conversions and poor selectivity to the product, primary alcohols. In contrast, typical selectivities using the process of the present invention, for example, in the reductive hydrolysis of adiponitrile to hexanediol or 2-methylglutaronitrile to methylpentanediol are comparatively very high, with only traces of amine by-products being formed.

Suitable nitrile substrates which are applicable in the reductive hydrolysis process of the present invention can be those having at least one CN group which is capable of being reduced to the corresponding primary alcohol. Typically, the substrate is a monomeric material with one or two CN groups. However, the substrate can also be oligo- or polymeric, with either regularly occurring or occasional CN functional groups, or mixtures comprising, for example, fluoronitriles such as, $F(CF_2CF_2)_zCH_2CH_2CN$, wherein z ranges from 2 to about 6.

Suitable nitrile substrates comprise the classes of linear or branched saturated aliphatic $C_2$–$C_{18}$ mono- and $C_3$–$C_{19}$ dinitriles and phenyl derivatives thereof, $C_4$–$C_{13}$ saturated alicyclic mono- and $C_5$–$C_{14}$ dinitriles, $C_3$–$C_{18}$ linear or branched olefinically unsaturated aliphatic nitriles, $C_6$–$C_{13}$ olefinically unsaturated alicyclic nitriles, $C_7$–$C_{14}$ aromatic mono- and dinitriles, $C_6$–$C_8$ heterocyclic nitrogen and oxygen mononitriles, $C_3$–$C_4$ cyanoalkanoic amides, $C_2$–$C_{12}$ saturated aliphatic cyanohydrins or hydroxynitriles, mixtures of the above-described nitriles, wherein said nitriles can also contain non-interfering substituents.

Examples of some substituents which generally do not interfere with the desired reduction reaction can be hydroxyl, amine, ether, alkyl, alkoxy, and aryloxy. For example, cyanohydrins and hydroxynitriles are both acceptable nitriles. Unsaturated, hydrogenatable substituents such as ketone, ester, amide, aldehyde, imine, nitro, alkene, and alkyne are permissible in that they do not interfere with the reductive hydrolysis of the nitrile group, but they may themselves be hydrogenated partly or completely in the course of the reductive hydrolysis. Carboxylic acids are generally not acceptable substituents since they react with the catalyst, deactivating it.

Representative examples of specific nitriles applicable in the invention process comprise: acetonitrile ($C_2$), propionitrile ($C_3$), butyronitrile ($C_4$), valeronitrile ($C_5$), capronitrile ($C_6$), 2,2-dimethylpropanenitrile, enanthonitrile ($C_7$), caprylonitrile ($C_8$), pelargononitrile ($C_9$), caprinitrile ($C_{10}$), hendecanenitrile ($C_{11}$), lauronitrile ($C_{12}$), tridecanenitrile ($C_{13}$), myristonitrile ($C_{14}$), pentadecanenitrile ($C_{15}$), palmitonitrile ($C_{16}$), margaronitrile ($C_{17}$), stearonitrile ($C_{18}$), phenylacetonitrile (benzyl nitrile), napthylacetonitrile, malononitrile, succinonitrile, glutaronitrile, 2-methylglutaronotrile, adiponitrile, acrylonitrile, methacrylonitrile, 2-methyleneglutaronitrile, 1,4-dicyano-2-butene, 1,4-dicyano-1-butene, dodecanedinitrile, 3-butenenitrile, 4-pentenenitrile, 3-pentenenitrile, 2-pentenenitrile, 2-hexenenitrile, 2-heptenenitrile, glycolonitrile (formaldehyde cyanohydrin), hydracrylonitrile (ethylene cyanohydrin), epicyanohydrin (gamma-cyanopropylene oxide), lactonitrile, pyruvonitrile, cyclohexanecarbonitrile, benzonitrile, o-tolylnitrile, m-tolylnitrile, p-tolylnitrile, anthranilonitrile, m-aminobenzonitrile, p-aminobenzonitrile, 1-napthonitrile, 2-napthonitrile, phthalonitrile, isophthalonitrile, terephthalonitrile, mandelonitrile, 2-pyridinenitrile, 3-pyridinenitrile, 4-pyridinenitrile, or 2-furylacetonitrile.

Preferred nitriles in the process are adiponitrile, 2-methylglutaronitrile, and dodecanedinitrile. Also preferred is 3-cyano methyl isobutyrate which cyclizes on reductive hydrolysis producing 2-methyl-butyrolactone, a useful intermediate for 3-methyl-tetrahydrofuran.

Water is a required reactant in the reductive hydrolysis. At least one mole of water is required per mole of nitrile, but larger amounts can be used, and quantities of 2000 moles water per mole nitrile or even more can be used. The preferred amount of water is from about 30 to about 300 moles water/mole nitrile. Larger amounts of water enhance selectivity to alcohols but make product isolation more difficult. Smaller amounts of water reduce the selectivity to alcohols, increasing the amount of amines produced. In the absence of water, these same catalysts can hydrogenate nitriles to amines.

Use of a solvent is preferred to facilitate contacting of the reactants and removal of heat. The solubility of the respective materials in the solvent (or mixture of solvents) should be significantly large enough to initiate and maintain the reductive hydrolysis process.

Solvents which are applicable in the invention process must be inert toward hydrogenation under the reaction conditions and possess adequate solvating ability for the substrate nitrile, catalyst and water.

Suitable solvents comprise $C_6$–$C_{12}$ non-fused benzenoid hydrocarbons and $C_2$–$C_{18}$ alkyl derivatives thereof, $C_5$–$C_{12}$ linear or branched saturated aliphatic or alicyclic hydrocarbons, $C_4$–$C_{12}$ saturated aliphatic cyclic mono- or diethers, or $C_7$–$C_{14}$ aromatic ethers, or mixtures thereof. By the term "non-fused benzenoid hydrocarbons" is meant that if more than one benzene ring is present in the hydrocarbon, the rings are isolated and not fused together. Thus, the term includes biphenyl, but not naphthalene.

Suitable solvents further comprise nitriles, amines, and alcohols, preferably the reductive hydrolysis substrates, intermediates and products of hydrogenation or reductive hydrolysis provided that the selected solvent is an adequate solvent for catalyst, substrate nitrile, and water as described below. Representative examples are acetonitrile, propionitrile, butyronitrile, propyl amine, butyl amine, methanol, ethanol, propanol, isopropanol, n-butanol, isobutanol, tert-butanol, 2,2-dimethylpropanol, ammonia, methylamine, ethylamine, n-propylamine, isopropylamine, n-butylamine, amylamine, azacycloheptane, 2-methylpentamethylenediamine and hexamethylenediamine, xylene, hexamethylbenzene, biphenyl, n-octadecylbenzene, benzene, toluene, pentane, cyclopentane, cyclohexane, methylcyclohexane, hexane, isoctane, decane, cyclodecane, tetrahydrofuran, p-dioxane, 2,5-dimethyltetrahydrofuran, methyl tetrahydrofurfuryl ether, dimethyl ether, 1,2-dimethoxyethane, diglyme, diethylether, diisopropyl ether, anisole, diphenylether, and mixtures thereof.

Preferred solvents are adiponitrile, 2-methylglutaronitrile, hexanediol, 2-methylpentanediol, ammonia, THF, t-butyl methyl ether, toluene, n-amylamine, n-butylamine, 2-methyl-pentamethylenediamine, and hexamethylenediamine.

It is essential that adequate water be available to the reacting nitrile to achieve the desired reductive hydrolysis, producing alcohol, rather than simple hydrogenation which would produce amine. There are three possible modes of operation: (a) neat, i.e., without any solvent other than starting nitrile or product alcohol, (b) with a water immiscible solvent, or (c) with a homogenizing solvent.

The preferred mode of operation depends on the nature of the nitrile being reacted, keeping in mind the necessity of providing adequate water for reductive hydrolysis to occur rather than simple reduction. The main criterion is the ability of the nitrile or product alcohol to dissolve the reactants (nitrile, catalyst, and water) sufficiently to enable reductive hydrolysis to occur.

"Hydrophilic" and some "amphiphilic" nitrile reactants, those which are liquid at reaction temperature and which are sufficiently good solvents for both catalyst and water at the reaction temperature for reductive hydrolysis to occur, are amenable to operation in the neat mode. Similarly, when the product alcohol is a good solvent for the starting nitrile, catalyst, and water, the product alcohol itself can be used as the solvent. Lower nitriles such as acetonitrile or propionitrile could thus use the product alcohol as the solvent. Adiponitrile and methylglutaronitrile, though not miscible with water at ambient temperature, become miscible at elevated temperatures, therefore, they can also be considered candidates for operation in the neat mode. Even nitriles which are not completely miscible with water are amenable to the neat mode provided they are capable of dissolving catalyst and sufficient water to favor reductive hydrolysis over simple hydrogenation.

The purpose of using a water-immiscible solvent is to facilitate recovery and recycle of catalyst in the case where the product alcohol is water soluble. This mode is feasible when the nitrile or product alcohol is a sufficiently good solvent for both catalyst and water to favor reductive hydrolysis over simple hydrogenation to amine. The water-soluble product can be separated from the water-insoluble catalyst by simple decantation and/or extraction procedures.

Suitable water-immiscible solvents comprise aliphatic and aromatic hydrocarbons, and water immiscible ethers. Preferred solvents are toluene and t-butyl methyl ether.

The water-immiscible solvent mode is not applicable with hydrophobic nitriles, e.g., dodecanedinitrile or alpha-methyl benzyl cyanide, due to insufficient contact with water, resulting in hydrogenation to amine rather than reductive hydrolysis.

With hydrophobic nitriles such as dodecanedinitrile or alpha-methyl benzyl cyanide, a homogenizing solvent is required. This solvent need not be miscible with water, but must be capable of dissolving nitrile, catalyst, and sufficient water to favor reductive hydrolysis over hydrogenation. The preferred solvents are the lower boiling alcohols and ethers, for example, dimethoxyethane, p-dioxane, tetrahydrofuran (THF), 2-methoxyethanol, 2-ethoxyethanol, and 2-butoxyethanol. THF is most preferred.

The catalyst for this process of the present invention is selected from the transition metal complex having the formula $MHZ(CO)L_n(PR_3)_2$ as described previously. Preferred transition metal complex catalysts comprise those having the formula $RuHCl(CO)(PCy_3)_2$, $RuH_2(CO)(H_2)(PCy_3)_2$, $RuHCl(CO)(P-iPr_3)_2$, or $RuH_2(CO)(H_2)(P-iPr_3)_2$, wherein Cy is a cyclohexyl group and iPr is an isopropyl group. The amount of catalyst used can vary from about 10 mole percent, based on nitrile to be hydrogenated, to about 0.01 mole percent. The preferred amount of catalyst is between about 1% and about 0.1% of the amount of nitrile to be hydrogenated on a molar basis. Larger or smaller amounts of catalyst can be used at the expense of catalyst cost or reaction time respectively. Excess phosphine can be present if desired and does not interfere with reductive hydrolysis. Although excess phosphine is not required, the presence of excess phosphine ensures that there is always adequate phosphine to stabilize the transition metal catalyst, even if adventitious oxygen oxidizes a small amount of phosphine to phosphine oxide or other side reactions degrade portions of the phosphine ligand. Phosphine oxide formed in this manner can also be present and does not interfere with the reductive hydrolysis reaction. The molar ratio of excess phosphine to transition metal can vary from zero to about 60 or even more. The preferred molar ratio is between zero and about 30, with a molar ratio of about 2 to about 25 being most preferred.

The reductive hydrolysis can be conducted at any convenient temperature, from about 0° C. to about 200° C. Lower temperatures require prolonged reaction times while higher temperatures reduce catalyst life and reduce the yield of the desired products. The preferred temperature is in the range of about 60° to about 120° C., with about 80° to about 100° C. being most preferred.

The source of hydrogen can be hydrogen gas or mixtures of hydrogen gas with other gases which do not interfere with the desired reductive hydrolysis. Non-interfering gases comprise, for example, inert gases, such as helium, argon, and nitrogen. Oxygen and carbon monoxide should be avoided since they can react with the catalysts.

The pressure employed can be from about 100 kPa (1 atmosphere) to about 15000 kPa or even higher. Elevated pressures are preferred since the solubility of hydrogen is increased which leads to higher reaction rates. However, pressures above 7000 kPa are generally avoided due to the high cost of equipment capable of operating at such pressures. The preferred pressure is in the range of about 800 kPa to about 7000 kPa.

The reductive hydrolysis of nitriles of the present invention is a two-phase reaction. Therefore, it is essential to provide adequate gas-liquid contact to enable the gaseous hydrogen to dissolve in the liquid reaction phase. Adequate gas-liquid contact can be facilitated by any of the various agitation methods familiar to those skilled in the art. Typical methods comprise sparging gas below the liquid surface in a tank reactor, stirring the liquid in a tank reactor to draw gas into the liquid and create bubbles, use of packing in a tower reactor to obtain high liquid surface area, or use of a bubble column reactor, wherein bubbles of gas are introduced into the reactor and rise through the liquid phase.

In another embodiment of the present invention, the compound $MHZ(CO)L_n(PR_3)_2$ as described previously, is used as a catalyst in a process for the selective reductive hydrolysis of a dinitrile to a hydroxynitrile. The dinitrile is contacted with gaseous hydrogen and water in the presence of the catalyst and subsequently agitated for an amount of time selected to favor yield of the hydroxynitrile over yield of a diol.

The dinitrile can be any aliphatic dinitrile comprising about 3 to about 19 carbon atoms, but preferably comprising about 6 to about 12 carbon atoms. Preferably, the carbon atoms are arranged in a linear or branched chain. Especially preferred examples of dinitriles are adiponitrile and dodecanedinitrile.

The amount of catalyst, excess phosphine, temperature, solvents and modes of operation, amounts of water, pressure, agitation requirements and sources of hydrogen are the same as discussed above for the reductive hydrolysis of nitriles.

The desired product of the selective reductive hydrolysis, a hydroxynitrile, is an intermediate in one embodiment of the present reductive hydrolysis process which eventually results in the formation of a diol. The hydroxynitrile concentration in the reacting mixture passes through a maximum as the reaction progresses. One objective of this embodiment of the present invention is to maximize the concentration of the hydroxynitrile in the reacting mixture at the highest possible conversion of the starting dinitrile. The yield of the hydroxynitrile and the position of the maximum with respect to dinitrile conversion depend on operating conditions such as temperature, hydrogen pressure, amount and kind of catalyst, dilution of starting dinitrile, as well as, the type of solvent. These variables in turn influence the optimum contact time for the reaction.

The optimum reaction time of the present invention needed to favor formation of the hydroxynitrile need be determined only once for any given set of reaction conditions. Once the optimum has been determined, it will remain constant as long as reaction conditions, such as catalyst, reactant concentrations, temperature, and pressure are held constant.

Another embodiment of the present invention is a simple process for separation of the ruthenium complex catalyst from reductive hydrolysis product compounds and recycle of the catalyst. Conventional methods of accomplishing such separations include fractional distillation, fractional crystallization, extraction, and chromatography. Distillation methods in particular are very commonly used, but the high temperature and sub-atmospheric pressure required, due to the relatively high boiling point of reductive hydrolysis products, may adversely affect catalyst stability.

Unlike most homogeneous catalysts, the catalysts of the present invention are unexpectedly stable in the presence of water. Therefore, in cases where the product compounds are soluble in water, and where a reaction solvent is employed which is immiscible with water, the product compounds can be separated from the catalyst and reaction solvent by extraction with water. The catalyst is essentially insoluble in water and remains dissolved in the reaction solvent while the water-soluble product compounds are removed into the water extracts. The resulting solution of catalyst in the reaction solvent, which can be dried if desired, is then recycled. The product compounds can be recovered from the water extracts by distillation or any other desired method, without concern for catalyst stability.

Advantages of separation by water extraction comprise simplicity, mild conditions, and low energy consumption. In particular, the extraction can be conducted at mild temperatures, between about 20° C. and about 100° C., and mild pressures, between about 100 kPa and about 500 kPa, which are desirable from the standpoint of maintaining catalyst stability.

EXAMPLES

General Procedures

| Abbreviations | |
|---|---|
| ACN | aminocapronitrile |
| ADN | adiponitrile |
| DMF | N,N-dimethyl formamide |
| iPr | isopropyl |
| HMD | hexamethylenediamine |
| HMI | hexamethyleneimine (aka azacycloheptane) |
| MGN | 2-methylglutaronitrile |
| MPDO | 2-methyl-1,5-pentanediol |
| MTBE | methyl t-butyl ether |
| THF | tetrahydrofuran |

Example 1

Preparation of $RuH_2(CO)(H_2)(P\text{-}iPR_3)_2$

This preparation requires $RuHCl(CO)(P\text{-}iPr_3)_2$, which was prepared according to Estreuelas and Werner, *J. Organomet. Chem.*, 1986, 303, 221. The following preparation of $RuH_2(H_2)(CO)(P\text{-}iPr_3)_2$ was adapted from Gusev, Vymenits, and Bakhmutov, *Inorg. Chem.*, 1992, 31, 2 and V. V. Grushin, A. B. Vymenits, M. E. Vol'pin, *J. Organomet. Chem.*, 1990, 382, 185. A mixture of 0.5 mmol $RuHCl(CO)(P\text{-}iPr_3)_2$ and 0.2 mmol benzyltriethyl-ammonium chloride in 35 mL toluene was placed in a Fisher-Porter tube. After adding 1 mL of 50% aqueous NaOH, the tube was pressurized to 860 kPa with $H_2$ and stirred for 1 hour. The temperature was increased to 50° C. for 1 hour, after which the reaction was cooled, brought into the glovebox, and allowed to settle. The toluene phase, containing the catalyst, was separated from the aqueous caustic phase, which was discarded. Solution IR of the toluene phase showed $v_{CO}$ at 1940 cm$^{-1}$. The toluene solution was used directly in reductive hydrolysis.

Example 2

Preparation of $RuHCl(CO)(PCy_3)_2$ $RuHCl(CO)(PCy_3)_2$ was first prepared by Moers and Langhout, *Recueil*, 1972, 91, 591. We found it more convenient to prepare it analogously to $RuHCl(CO)(P\text{-}iPr_3)_2$. Thus, a mixture of 2.0 g $RuCl_3(H_2O)_x$ (1.4% water, 9.5 mmol Ru), 10.6 g $PCy_3$ (37.8 mmol, 4P/Ru), and 75 mL methanol was refluxed for a total of 18 h over three days, then allowed to settle overnight. The yellow-orange solid product was collected on a frit, rinsed with methanol, then ether, and dried in vacuo. Yield: 6 g (87%). $^{31}P\{^1H\}$: 44.0 (s). $^1H$: −24.2 (t, 1H, hydride), 1–2 (66H, cyclohexyl protons). IR (Nujol): 1906 (vs, $v_{CO}$), 2061 (w, $v_{RuH}$).

Example 3

Preparation of $RuH_2(CO)(H_2)(PCy_3)_2$

This is a new compound, prepared by analogy with the P-iPr$_3$ complex above.

A mixture of 0.5 mmol $RuHCl(CO)(PCy_3)_2$ and 0.2 mmol benzyltriethylammonium chloride in 35 mL toluene was placed in a Fisher-Porter tube. After adding 1 mL of 50% aqueous NaOH, the tube was pressurized to 860 kPa with $H_2$, heated to 50° C., and stirred for 2 hours. The reaction was cooled, brought into the glovebox, and allowed to settle. Solution IR of the toluene phase showed $v_{CO}$ at 1936 cm$^{-1}$. Some unreacted starting material was present, as evidenced by its $v_{CO}$ band at 1902 cm$^{-1}$. The toluene solution was used directly in reductive hydrolysis.

Example 4

MGN reductive hydrolysis using $RuHCl(CO)(PCy_3)_2$

A mixture of 0.1 mmol $RuHCl(CO)(PCy_3)_2$, 5.5 mmol MGN, 20.4 g water and 13.46 g THF was stirred in an autoclave at 80° C. under 7000 kPa $H_2$. After 5.6 hours, gas chromatography (gc) analysis using an internal standard method showed that all the MGN had been consumed and the yield of 2-methyl-1,5-pentanediol was 97%.

Example 5

MGN reductive hydrolysis using $RuHCl(CO)(P\text{-}iPR_3)_2$

A mixture of 0.1 mmol catalyst, 5.5 mmol MGN, 17.7 g THF, 16.3 g water, and 0.11 g cyclododecane (internal standard for gc analysis) was stirred in an autoclave and heated to 80° C. under 7000 kPa $H_2$. After 4 hours, gc analysis showed a 96% yield of 2-methylpentanediol.

Example 6

MGN reductive hydrolysis using $RuH_2(CO)(H_2)(P\text{-}iPR_3)_2$

A mixture of 0.1 mmol catalyst (stock solution in toluene), 5.2 mmol MGN, 15.2 g methyl t-butyl ether (MTBE), 15.2 g water, and 0.16 g cyclododecane (internal standard for gc analysis) was stirred in an autoclave and heated to 80° C. under 7000 kPa $H_2$. After 5 hours, gc analysis showed a 98% yield of 2-methylpentanediol.

Example 7

β-hydroxy-undecenenitrile reductive hydrolysis using $RuHCl(CO)(PCy_3)_2$

A mixture of 0.1 mmol catalyst, 2.76 mmol nitrile, 15.4 g water, 17.7 g THF, and 0.1251 g cyclododecane (gc internal standard) was stirred in an autoclave and heated to 80° C. under 7000 kPa $H_2$. After 1 hour, gc analysis showed that all the nitrile had been converted to 1,3-undecanediol.

Example 8

Reductive Hydrolysis of Oligomeric Polyfluoroalkane Nitrile

Oligomeric polyfluoroalkane nitrile is a mixture of oligomeric nitriles with fluorocarbon backbones, $F(CF_2CF_2)_z$ $CH_2CH_2CN$, wherein z=2 to 6.

The mixture used in this example contained about 27% z=2, 46% z=3, 23% z=4 and 5% z=5 oligomers.

A mixture of 0.1 mmol $RuHCl(CO)(PCy_3)_2$, 9.87 mmol oligomeric polyfluoroalkane nitrile, 13.29 g THF, and 18.3 g water was heated in a stirred autoclave at 100° C. under 7000 kPa $H_2$. After 4.4 h, gc analysis showed complete conversion of the starting nitriles to a mixture of the corresponding amines and primary alcohols. Alcohol products predominated, with the alcohol/amine ratio varying from 1.7 (z=2) to 9.6 (z=4).

Example 9

Reductive Hydrolysis with Catalyst Recycle

A mixture of 0.1066 mmol $RuHCl(CO)(PCy_3)_2$, 20.5 mmol MGN, 11.37 g MTBE, and 15.23 g water was heated in a stirred autoclave to 100° C. under 7000 kPa $H_2$. After 5.5 h, the reaction was cooled and the pressure vented. The MTBE and water phases were separated by decantation. The water phase was extracted with 5 mL fresh MTBE, which was combined with the original MTBE phase. Analysis of the aqueous phase showed 6.5 mmol MPDO and 2.75 mmol hydroxynitriles.

The MTBE phase, containing recycle catalyst, unconverted MGN, and remaining intermediates not removed in the water phase, was recycled by adding 20.39 mmol MGN and 15.9 g water. After 7.2 hours, the reaction was treated as above. The aqueous phase contained 8.3 mmol MPDO and 3.4 mmol hydroxynitriles. The MTBE phase was analyzed and recycled again, adding less fresh MGN to achieve higher conversion.

The MTBE phase, containing recycle catalyst, 0.81 mmol unconverted MGN, 2.78 mmol hydroxynitrile, and 1.98 mmol MPDO not removed in the water phase above, was recycled by adding 5.36 mmol fresh MGN and 14.7 g water. A total of ≈10.93 mmol $C_6$ materials was charged. After 7.9 hours, the reaction was worked up as before. The aqueous phase contained 8.4 mmol MPDO, 1.26 mmol hydroxynitriles, and a trace of MGN. The organic phase contained 1.77 mmol MPDO, 0.99 mmol hydroxynitrile, and 0.13 mmol MGN. A total of 12.55 mmol $C_6$ products were found, giving a mass balance of 115%.

The MTBE phase above was used a fourth time, adding 5.2 mmol fresh MGN and 15.4 g water. After 7.5 h at 100° C. and 7000 kPa $H_2$ and workup as before, the MGN was completely converted. The final product mixture contained a total of 95% MPDO and 5% hydroxynitrile (normalized to 100% total). The final mass balance was ≈115%.

A similar recycle series using toluene/water instead of MTBE/water gave, on the fifth use, 100% conversion of MGN with a 98% yield of MPDO and a mass balance of 110%.

Comparative Example A

Reductive Hydrolysis with Raney Ni

A mixture of 0.2 g water-wet Cr-promoted Raney Ni (W. R. Grace's "2400"), 0.60 g ADN, 30 mL water, and 5 mL toluene was heated to 80° C. in a Fisher-Porter tube under 860 kPa $H_2$. After 8.1 h, the ADN was completely consumed. The main products were ACN, HMD, and HMI. No hexanediol was detected.

Comparative Example B

Reductive Hydrolysis with Palladium on carbon (Pd/C)

A mixture of 5 mmol ADN, 1.1 g 0.5% Pd/C, 15 g water and 17 g toluene was heated to 120° C. in a Fisher-Porter tube pressurized to 860 kPa with hydrogen. After 6.3 h, gc analysis showed that 96% of the ADN had been converted. The major product was tris(5-cyanopentyl)amine (about 58%) with lesser amounts of di(5-cyanopentyl)amine (14%) and 5-cyanopentyl HMI (14%). Only a trace of ACN was observed. No significant amount of alcohol was formed.

Comparative Example C

Reductive Hydrolysis with Rh/MgO

A sample of Rh/MgO was prepared according to the procedure described in U.S. Pat. No. 4,389,348 and U.S. Pat. No. 4,601,859. A mixture of 0.25 g of the Rh catalyst, 0.58 g ADN, 15 mL water and 20 mL THF was stirred and heated in a Fisher-Porter tube at 80° C. under 860 kPa $H_2$. After 3.8 hours, gc analysis showed 82% ADN, 5% ACN, and 1% hydroxycapronitrile, as well as other products. The low conversion showed the relatively low activity of this catalyst, and the 5:1 ratio of ACN:hydroxynitrile showed that hydrogenation predominated over reductive hydrolysis.

What is claimed is:

1. A process for the reductive hydrolysis of an organic nitrile, comprising the steps of:

(a) contacting said nitrile with gaseous hydrogen and water in the presence of a catalyst having the formula $MHZ(CO)L_n(PR_3)_2$, wherein:

M is a transition metal selected from the group consisting of: Fe, Ru and Os;

Z is a formally anionic ligand selected from the group consisting of: H, halogen, R, C(O)R, OC(O)R, $CO_2R$, CN, $NR_2$ and OR;

L is a neutral ligand selected from the group consisting of: $H_2$; $N_2$; CO; a monofunctional compound selected from the group consisting of: nitriles, amines, alcohols, ethers, esters, amides, alkenes, alkynes, aldehydes, ketones and imines; and a multifunctional compound containing at least two functional groups independently derived from the monofunctional compounds;

$(PR_3)_2$ represents phosphine ligands present as either separate ligands or cojoined together;

each R is a substituent independently selected from the group consisting of: H; and a hydrocarbyl group, optionally substituted with one or more halo, hydrocarbyloxy, hydrocarbylamino or dihydrocarbylamino groups; and n is 0 or 1; and (b) subsequently agitating the nitrile, water, hydrogen and catalyst to form an alcohol.

2. The process of claim 1 wherein contact is made at a temperature of about 0° C. to about 200° C. at a pressure of about 100 kPa to about 15000 kPa, optionally in the presence of a water-immiscible solvent or a homogenizing solvent.

3. The process of claim 2 wherein the solvent is a substrate, an intermediate or a product of the reductive hydrolysis.

4. The process of claim 1 wherein the amount of water in step (a) is at least 1 mole of water per mole of nitrile.

5. The process of claim 1 wherein the amount of water in step (a) is at least 30 to about 300 moles of water per mole of nitrile.

6. The process of claim 2 wherein the alcohol product is water-soluble and wherein the solvent is immiscible with water, further comprising separating the alcohol product from the solvent and the catalyst by extraction with water and recycling the catalyst and the solvent.

7. The process of claim 1 wherein the nitrile is selected from the group consisting of: adiponitrile, 2-methylglutaronitrile, 3-cyano-methylisobutyrate and dodecanedinitrile.

8. The process of claim 1 wherein the organic nitrile is a dinitrile and the alcohol is a diol.

9. The process of claim 1 wherein L is a substrate, an intermediate or a product of the reductive hydrolysis.

10. The process of claim 1 wherein the catalyst is selected from the group consisting of transition metal complexes wherein M is Ru, and Z is H or halogen.

11. The process of claim 10 wherein the catalyst is selected from the group consisting of: $RuHCl(CO)(P-iPr_3)_2$, $RuHCl(CO)(PCy_3)_2$, $RuH_2(CO)(H_2)(P-iPr_3)_2$, and $RuH_2(CO)(H_2)(PCy_3)_2$.

12. A process for the selective reductive hydrolysis of a dinitrile, comprising the steps of:

(a) contacting said dinitrile with gaseous hydrogen and water in the presence of a catalyst having the formula $MHZ(CO)L_n(PR_3)_2$, wherein:

M is a transition metal selected from the group consisting of: Fe, Ru and Os;

Z is a formally anionic ligand selected from the group consisting of: H, halogen, R, C(O)R, OC(O)R, $CO_2R$, CN, $NR_2$, and OR;

L is a neutral ligand selected from the group consisting of: $H_2$; $N_2$; CO; a monofunctional compound selected from the group consisting of: nitriles, amines, alcohols, ethers, esters, amides, alkenes, alkynes, aldehydes, ketones and imines; and a multifunctional compound containing at least two functional groups independently derived from the monofunctional compounds;

$(PR_3)_2$ represents phosphine ligands present as either separate ligands or cojoined together;

each R is a substituent independently selected from the group consisting of: H; and a hydrocarbyl group, optionally substituted with one or more halo, hydrocarbyloxy, hydrocarbylamino or dihydrocarbylamino groups; and n is 0 or 1; and (b) subsequently agitating the dinitrile, hydrogen, water and catalyst for an amount of time selected to favor yield of a hydroxynitrile over yield of a diol.

13. The process of claim 12 wherein contact is made at a temperature of about 0° C. to about 200° C. at a pressure of about 100 kPa to about 15000 kPa, optionally in the presence of a water-immiscible solvent or a homogenizing solvent.

14. The process of claim 13 wherein the solvent is a substrate, an intermediate or a product of the selective reductive hydrolysis.

15. The process of claim 12 wherein the amount of water in step (a) is at least 1 mole of water per mole of dinitrile.

16. The process of claim 15 wherein the amount of water in step (a) is at least 30 moles of water per 300 moles of dinitrile.

17. The process of claim 13 wherein the hydroxynitrile is water-soluble and wherein the solvent is immiscible with water, further comprising separating the hydroxynitrile product from the solvent and the catalyst by extraction with water and recycling the catalyst and the solvent.

18. The process of claim 12 wherein the dinitrile is selected from the group consisting of: adiponitrile and dodecanedinitrile.

19. The process of claim 12 where L is a substrate, an intermediate or a product of the selective reductive hydrolysis.

20. The process of claim 12 wherein the catalyst is selected from the group consisting of transition metal complexes wherein M is Ru, and Z is H or halogen.

21. The process of claim 20 wherein the catalyst is selected from the group consisting of: $RuHCl(CO)(P-iPr_3)_2$, $RuHCl(CO)(PCy_3)_2$, $RuH_2(CO)(H_2)(P-iPr_3)_2$, and $RuH_2(CO)(H_2)(PCy_3)_2$.

* * * * *